(12) United States Patent
Lee et al.

(10) Patent No.: US 10,137,159 B2
(45) Date of Patent: Nov. 27, 2018

(54) BOEHMERIA EXTRACT AND ITS USE IN TREATING LIVER DISEASES

(71) Applicant: Industrial Technology Research Institute, Hsin Chu (TW)

(72) Inventors: Lain-Tze Lee, Hsinchu (TW); Ying-Chu Shih, Hsinchu County (TW); Hui-Ping Tsai, Hsinchu (TW); Meng-Nan Lin, Taichung County (TW); Wan-Chun Liu, Hsinchu County (TW)

(73) Assignee: Industrial Technology Research Institute, Hsinchu (TW)

(*) Notice: Subject to any disclaimer, the term of this patent is extended or adjusted under 35 U.S.C. 154(b) by 52 days.

(21) Appl. No.: 14/087,717

(22) Filed: Nov. 22, 2013

(65) Prior Publication Data

US 2014/0079818 A1  Mar. 20, 2014

Related U.S. Application Data

(63) Continuation of application No. 12/978,756, filed on Dec. 27, 2010, now abandoned.

(51) Int. Cl.
 *A61K 36/185* (2006.01)

(52) U.S. Cl.
 CPC ...... *A61K 36/185* (2013.01); *A61K 2236/331* (2013.01)

(58) Field of Classification Search
 None
 See application file for complete search history.

(56) References Cited

U.S. PATENT DOCUMENTS

| 7,431,946 B2 * | 10/2008 | Pan et al. | 424/725 |
| 2010/0093601 A1 * | 4/2010 | Tyler et al. | 514/2 |
| 2010/0168221 A1 * | 7/2010 | Lee et al. | 514/456 |
| 2011/0212541 A1 * | 9/2011 | Tyler et al. | 436/501 |

FOREIGN PATENT DOCUMENTS

| CN | 1634212 A | | 6/2005 |
| JP | 2005194256 A | * | 7/2005 |
| KR | 20050104970 A | * | 11/2005 |

OTHER PUBLICATIONS

Saracyn, et al., "D-Galactosamine Intoxication in Experimental Animals: Is it Only an Experimental Model of Acute Liver Failure?", Med Sci Monit, 2015; 21: 1469-1477.

* cited by examiner

*Primary Examiner* — Amy L Clark
(74) *Attorney, Agent, or Firm* — Cesari and McKenna, LLP

(57) ABSTRACT

A method for treating liver fibrosis. The method includes administering to a subject suffering from liver fibrosis a pharmaceutically active extract obtained from a *Boehmeria* species. Also disclosed is a method for regenerating liver tissue and a method for improving a liver function.

11 Claims, No Drawings

BOEHMERIA EXTRACT AND ITS USE IN TREATING LIVER DISEASES

CROSS-REFERENCE TO RELATED APPLICATION

This application is a continuation of U.S. patent application Ser. No. 12/978,756, filed on Dec. 27, 2010.

BACKGROUND

The liver, a vital organ, plays a major role in metabolism of breaking down or modifying toxic substances. It also performs other important function, e.g., glycogen storage, hormone production, plasma protein synthesis, and red blood cell decomposition.

Life-threatening liver conditions include liver cirrhosis, liver viral infection, and liver cancer, which are initiated by liver inflammation and/or liver fibrosis There is an urgent need in enhancing liver function and treating liver conditions.

SUMMARY

This invention is based on an unexpected discovery that a cold water extract of a *Boehmeria* species exhibits high efficacy in improving liver functions.

Thus, one aspect of this invention relates to a pharmaceutical composition prepared by an extracting process in which a *Boehmeria* species (e.g., *Boehmeria nivea* or *Boehmeria frustescens thunberg*) is the only herb subjected to extraction. The process includes immersing a part of a *Boehmeria* species in water at a pre-determined temperature for a pre-determined duration (e.g., at a temperature of 20-70° C. or 25-40° C. for 2-24 hours), removing the part of the *Boehmeria* species to obtain a solution, and concentrating the solution. The thus-obtained composition, containing active components extracted from the *Boehmeria* species, exhibits efficacy in improving liver functions. The extracting process may further include enriching the active components in the concentrated solution by chromatography (e.g., column chromatography or high performance liquid chromatography) to afford an even more efficacious pharmaceutical composition. The eluent used in the chromatography may include one or more of $H_2O$, $CH_3CN$, $CH_3OH$, and other suitable organic solvents (e.g., $H_2O$, $H_2O$—$CH_3CN$, or $H_2O$—$CH_3OH$).

Another aspect of this invention relates to a method of treating liver disease by administering to a subject in need thereof an effective amount of the above-described pharmaceutical composition.

Also within the scope of this invention is use of the pharmaceutical composition described above for improving liver function, treating liver disease, or promoting regeneration of liver tissues or for manufacturing of a medicament in the above-mentioned improvement/treatment/promotion.

The details of many embodiments of the invention are set forth in the description below. Other features, objects, and advantages of the invention will be apparent from the description and the claims.

DESCRIPTION

The pharmaceutical composition of this invention is prepared by extracting roots, stems, leaves, or flowers of a *Boehmeria* plant with an aqueous solution. *Boehmeria* is a genus consisting of about 100 species of flowering plants in the nettle family Urticaceae, native to Asia and North America. The species in this genus include, e.g., *Boehmeria biloba, Boehmeria boninensis, Boehmeria cylindrica, Boehmeria excelsa, Boehmeria frustescens thunberg, Boehmeria grandis, Boehmeria jamaicensis, Boehmeria nivea, Boehmeria platanifolia, Boehmeria stipularis*, and *Boehmeria tenacissima*. Described below is an exemplary extracting process for preparing a *Boehmeria nivea* composition:

Dry roots of *Boehmeria nivea* are immersed in water at 20-70° C. (or 25-40° C.). The water used has a purity of 90% or higher. It may contain a small amount(s) (i.e., <10%) of an organic solvent(s), such as methanol, ethanol, acetone, and acetonitrile.

The immersing duration varies. It can be 2 hours to 7 days, depending on the extracting solvent and temperature. After the immersion, the plant roots are removed and the solvent is concentrated to provide a crude extract product. One can rinse the crude extract to remove certain impurities. For example, the crude product is first dissolved in a polar solvent, such as alcohol, water, or a mixture thereof, and the resulting solution is then rinsed with an apolar solvent, e.g., n-hexane, to remove lipid or other apolar substances or rinsed with chloroform or ethyl acetate to remove small phenol compounds. Finally the rinsed solution is concentrated to dryness to afford a partially purified product.

One can also use chromatography to enrich active components that exhibit efficacy in improving liver functions. Chromatography technologies include paper chromatography, thin layer chromatography, column chromatography, gas chorography, and liquid chromatography (e.g., high performance liquid chromatography). Suitable eluent solvents include, but are not limited to water, methanol ($CH_3OH$), acetonitrile ($CH_3CN$), and a mixture thereof. A gradient eluent system can be used. Alternatively, one can also use recrystallization to enrich one or more active components. The recrystallization solvent can be an inorganic or organic solvent, e.g., a solvent in which the desired product has a low solubility at a low temperature, but has a higher solubility at a high temperature. It can also be a solvent pair or a mixture. An even more purified product can be thus obtained.

The structures of the active components and their purities can be determined using chromatography or other instruments, such as UV or NMR.

A thus-obtained product(s) can be stored at an ambient temperature or a lowered temperature and under a protective gas(es), e.g. nitrogen, argon, or helium.

An effective amount of the above-obtained pharmaceutically active preparation can be used to improve liver function, treat liver fibrosis, liver cirrhosis, liver inflammation, liver infection, and liver cancer, and regenerate damaged liver tissues.

The term "improving a liver function" refers to administering the preparation to a subject, whether or not having liver disease, to enhance his or her liver's capability of metabolism, glycogen storage, decomposition of red blood cells, plasma protein synthesis, hormone production, or detoxification. The term "treating liver disease" refers to administering the preparation to a subject who has a condition of liver fibrosis, liver cirrhosis, liver inflammation, liver viral infection (e.g., hepatitis B or C virus infection), or liver cancer, or has a symptom of the condition, or has a predisposition toward the condition, with the purpose to cure, heal, alleviate, relieve, alter, remedy, ameliorate, improve, or affect the condition, the symptoms of the condition, or the predisposition toward the condition. The term "regenerating liver tissues" refers to administering the preparation to a subject whose liver has been damaged by disease, alcohol, drugs, or other causes to promote regeneration of liver tissues to reverse the liver damage. The term "an effective amount" refers to the amount of the preparation that is required to confer one of the above-described effects on the subject. The effective amount varies, as recognized by those skilled in the art, depending on the types of the effects, route of administration, excipient usage, and the possibility of co-usage with other treatment.

To practice the method of the present invention, a composition containing one or more of the polymeric compounds described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The effects of a compound can be tested by an in vitro or in vivo assay. For example, compounds of this invention can be preliminarily screened by in vitro assays in which the compounds are tested for their bioactivity relating to liver function. Compounds that demonstrate high efficacy in the preliminary screening can be further evaluated by in vivo methods well known in the art to evaluate their activity in treating liver conditions, e.g., liver cancer.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

1 Preparation of Botanical Extracts

Roots of *Boehmeria nivea* L. Gaud. (2.5 kg) were immersed in water (50 L) at room temperature overnight. After the roots were removed, the solvent was concentrated to a mixture containing approximately 20% solid content to give 682 g of an extract product BL-01-01 (concentrated solution), which contained approximately 20% by weight solid content. A portion of the concentrated extract solution was freeze-dried to give dry solid product.

The isolated roots were immersed in water (50 L) overnight and the solvent was then removed. This process was repeated. The roots were refluxed in water (50 L) for 5 hours and then cooled to room temperature. After removed from the solvent, the roots were refluxed again in the same manner. The extracting solvents from the two refluxing processes were combined and freeze-dried to provide 96 g of a dry extract product (BL-01-12).

Roots of *Boehmeria nivea* L. Gaud. (20 g) were refluxed in water (400 mL) for 5 hours, and then cooled to room temperature. After the roots were removed, the extracting solvent was freeze-dried to provide 3.17 g of an extract product (BL-02).

2 Biological Assays 2.1 Experimental Materials and Methods

Male Sprague Dawley rats were quarantined for 1 week. The rat strain has shown to be a suitable animal model for testing liver fibrosis induced by carbon tetrachloride ($CCl_4$). Three rats were kept (3 per cage) in a temperature-controlled (23±2° C.) 40-70% humidity room with a 12-hour light-dark cycle. They were allowed to freely access rat chow and water.

8 week-old animals were used for testing liver fibrosis treatment. These animals were closely observed and recorded for unusual symptoms or death. Dead animals were dissected to assess causes.

Except for three animals used as control, the animals were divided into six treatment groups, each group including eight, and injected intraperitoneally 0.4 ml/kg of $CCl_4$ (e.g., 1.67 ml/kg 24% $CCl_4$ in olive oil) twice a week. Each treatment group was also administered daily by gavage for 8 weeks with one of the followings: (1) solvent, (2) Silymarin 200 mg/kg, (3) BL-01-12 100 mg/kg, (4) BL-01-12 300 mg/kg, (5) BL-01-12 900 mg/kg, and (6) BL-01-01 300 mg/kg.

Blood samples (0.3 ml each) were drawn from the tails of control and treated animals once before the $CCl_4$ injection and once every two weeks after the injection till 8th week. The blood samples were maintained at room temperature for 1 hour and centrifuged for 10 min at 6000 rpm at 25° C. to obtain serum. The serum was assayed using a chemical analyzer (Kodak Ektachem DT60 II) for alanine aminotransferase (ALT) and aspartate aminotransferease (AST) activities. Of note, ALT and AST levels in blood are indicators of liver functions. See Clinical Laboratory Medicine, Ed. by Kenneth McClatchey, Lippincott Williams & Wilkins, 2002, page 288.

At the end of the 8th week, all the control and treated animals were sacrificed. The left leaf of the liver from each animal was fixed in a 10% formalin solution. The fixed liver tissue was dehydrated in the following order with 30, 50, 70, 95, 99.5% ethanol, and xylene until it became transparent. Xylene was replaced with paraffin. The paraffin-embedded samples were sectioned into 5 µm-thick slices, each of which was placed on a glass slide and dried at 37° C. for collagen staining by the Sirius & Fast green staining method described below.

The liver slides were treated with xylene three times, each for three minutes, to remove paraffin and then rehydrated in the following order with 100, 100, 90, 70, 50% ethanol, and TBST (three minutes each). The rehydrated slides were stained with 0.1% Sirius red and 0.1% Fast green for one hour. After staining, the slides were subjected to another process of dehydration in the following order with 50%, 70%, 90%, 100%, and 100% ethanol (ten second each). They were further treated with xylene three times and became transparent. The transparent, stained liver slides were mounted with gel and stored for subsequent evaluation of liver fibrosis.

The mounted slides were examined under Olympus DT70-BX51 microscope and photographed. Liver fibrosis can be assessed based on Metavir Scoring system of five grades: (F0) no fibrosis, (F1) portal fibrosis without septa, (F2) portal fibrosis with few septa, (F3) numerous septa without cirrhosis, and (F4) cirrhosis, as described in Boigk et al., Hepatology, 1997, 26: 643-649; and Ruwart et al., Hepatology, 1989, 10: 801-806.

A student's t-test was used to determine significance. Statistical significance was assumed at values of $P<0.05$.

2.2 Results

AST and ALT values were analyzed for the blood samples taken from the control animals and those in the Groups treated with (1) solvent, (2) Silymarin 200 mg/kg, (3) BL-01-12 100 mg/kg, (4) BL-01-12 300 mg/kg, (5) BL-01-12 900 mg/kg; and (6) BL-01-01 300 mg/kg.

At week 4, the blood samples from Groups (2)-(5) had substantial increase in average values of AST compared with those at week 2, but no such change observed with those in the blood samples from Groups (1) and (6). At week 6, the average AST values were significantly lower in the blood samples from Groups (5) and (6) compared with that in the blood samples from Group (1) and the average AST value was substantially lower in the blood samples from Group (4) than that in the blood samples from Group (3), which was much lower than those in the blood samples from Groups (1) and (2). At week 8, the average AST values in all of the treated samples were dropped close to the normal value in the control samples.

At week 4, the blood samples from Groups (2), (4), and (5) had substantial increase in average ALT values from those at week 2, but no such change observed with those in the blood samples from Groups (1), (3), and (6). At week 6, the average ALT value was significantly lower in the blood samples from Group (6) in comparison with that in the blood samples from Group (1) and the average ALT values in the blood samples from Group (4) and (5) were substantially lower than that in the blood samples from Group (3), which was much lowered than those in the blood samples from Groups (1) and (2). At week 8, the average ALT values from the treated blood samples were reduced from those at week 6, approaching to the normal value in the control samples.

At week 4, the blood samples of Groups (1)-(6) had substantial decreases in average AST/ALT ratios from those at week 2; among the blood samples of these six groups, the average ratios were significantly lower in the blood samples from Groups (2), (4), and (5) than that in the blood samples from Group (1) and the control samples. At week 6, the average ratios in the blood samples from Groups (4)-(6) had substantially increases from week 4 and they were significantly higher than those in the blood samples from Group (1). The significantly higher AST/ALT ratios suggest that the $CCl_4$-induced liver inflammation in the animals from Groups (4)-(6) be significantly reduced at week 6.

At week 8, the ratios of the treated samples increased from those at week 6 and, among them, only the blood samples from Group (6) had a ratio significantly higher than those from Group (1).

Based on pathological examination of liver tissues harvested at the end of the eight-week long experiment, the animals of Group (6) had substantially less liver fibrosis than the animals of Groups (1)-(5). The Group (6) animals were treated with test substance BL-01-01. Thus, BL-01-01 showed an unexpected superior effect on preventing liver fibrosis.

In addition, male Sprague Dawley rats were used as an animal model for testing acute liver inflammation caused by thioacetamide (TAA). Groups of rats were treated with (1) 5 ml/kg TAA and 300 mg/kg BL-01-01 (solution), (2) 5 ml/kg TAA and 300 mg/kg BL-01-01 (freeze-dried), and (3) 5 ml/kg TAA and 500 mg/kg BL-02 (freeze-dried) and their blood samples were analyzed to determine the AST and ALT values in a manner similar to that described above.

The results show that BL-01-01(concentrated solution) significantly inhibited AST value increase at 24 and 48 hours after treatment of TAA; BL-01-01(freeze-dried) group significantly inhibited ALT value increase at 24 and 48 hours after treatment of TAA; and BL-02 did not significantly inhibit AST or ALT value increase after treatment of TAA. Thus, BL-01-01(solution) and BL-01-01(freeze-dried) are superior to BL-02 in treating acute liver inflammation.

3 Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating liver fibrosis, the method comprising:
   identifying a subject suffering from liver fibrosis;
   providing a pharmaceutically active extract obtained from *Boehmeria nivea*; and
   administering an effective amount of the pharmaceutically active extract to the subject,
wherein the pharmaceutically active extract is obtained by immersing a root of the *Boehmeria nivea* in water at 25° C.-40° C., removing the root to obtain a solution, and concentrating the solution to form the pharmaceutically active extract; and the pharmaceutically active extract is the only extract from *Boehmeria nivea* that is administered to the subject.

2. The method of claim 1, wherein the immersing step is performed for 2-24 hours.

3. The method of claim 1, wherein the solution is concentrated to a solid content of at least 20% by weight.

4. A method for regenerating liver tissue in a subject, the method comprising:
   identifying a subject in need of liver tissue regeneration;
   providing a pharmaceutically active extract obtained from *Boehmeria nivea*; and
   administering an effective amount of the pharmaceutically active extract to the subject,
wherein the pharmaceutically active extract is obtained by immersing a root of the *Boehmeria nivea* in water at 25° C.-40° C., removing the root to obtain a solution, and concentrating the solution to form the pharmaceutically active extract; and the pharmaceutically active extract is the only extract from *Boehmeria nivea* that is administered to the subject.

5. The method of claim 4, wherein the immersing step is performed for 2-24 hours.

6. The method of claim 4, wherein the solution is concentrated such that it has a solids content of at least 20% by weight.

7. The method of claim 5, wherein the subject has liver tissue damaged by alcohol or a drug.

8. The method of claim 4, wherein the subject has liver tissue damaged by alcohol or a drug.

9. A method for improving liver function in a subject in need thereof, the method comprising:
   providing a pharmaceutically active extract obtained from *Boehmeria nivea*; and
   administering an effective amount of the pharmaceutically active extract to the subject,
wherein the pharmaceutically active extract is obtained by immersing a root of the *Boehmeria nivea* in water at 25° C.-40° C., removing the root to obtain a solution, and concentrating the solution to form the pharmaceutically active extract; and the pharmaceutically active extract is the only extract from *Boehmeria nivea* that is administered to the subject.

10. The method of claim 9, wherein the immersing step is performed for 2-24 hours, and the solution is concentrated to a solid content of at least 20% by weight.

11. The method of claim 9, wherein the liver function is metabolism, glycogen storage, decomposition of red blood cells, plasma protein synthesis, hormone production, or detoxification.

* * * * *